United States Patent [19]

Uekama et al.

[11] Patent Number: 4,565,807

[45] Date of Patent: Jan. 21, 1986

[54] MEDICINAL COMPOSITION CONTAINING PIRPROFEN AND CYCLODEXTRIN AND A METHOD OF USE

[75] Inventors: Kaneto Uekama, Kumamoto; Mikio Hanafusa, Sanda; Masashi Tatsumi, Takatsuki; Tohru Hibi, Toyonaka, all of Japan

[73] Assignee: Ciba-Geigy Corporation, Ardsley, N.Y.

[21] Appl. No.: 512,793

[22] Filed: Jul. 11, 1983

[30] Foreign Application Priority Data

Jul. 19, 1982 [JP] Japan .................................. 57-125559

[51] Int. Cl.$^4$ ........................ A61K 31/73; C08B 37/16
[52] U.S. Cl. ....................................... 514/58; 536/46; 536/103
[58] Field of Search .................. 424/180; 536/103, 46; 514/58

[56] References Cited

U.S. PATENT DOCUMENTS

| | | | |
|---|---|---|---|
| 4,228,160 | 10/1980 | Szejtli et al. | 424/180 |
| 4,407,795 | 10/1983 | Nicolau et al. | 424/180 |
| 4,438,106 | 3/1984 | Wagu et al. | 424/180 |
| 4,451,457 | 5/1984 | Yoshikumi et al. | 424/180 |

OTHER PUBLICATIONS

Carney et al., "Chem. Abst.", vol. 79, 1973, p. 115390(a).
Tsurumi et al., "Chem. Abst.", vol. 97, 1982, p. 207950(h).

*Primary Examiner*—Johnnie R. Brown
*Attorney, Agent, or Firm*—Michael W. Glynn

[57] ABSTRACT

The invention relates to a new medicinal composition containing α-[3-chloro-4-(3-pyrrolin-1-yl)-phenyl]-propionic acid as the pharmacologically active ingredient, having analgesic and antiinflammatory properties, which composition has markedly improved properties, particularly with respect to taste and stability.

13 Claims, No Drawings

MEDICINAL COMPOSITION CONTAINING PIRPROFEN AND CYCLODEXTRIN AND A METHOD OF USE

The present invention relates to a new medicinal composition containing α-[3-chloro-4-(3-pyrrolin-1-yl)-phenyl]-propionic acid (hereinafter referred to as "Pirprofen") as the pharmacologically active ingredient, having analgesic and antiinflammatory properties, which composition has markedly improved properties, particularly with respect to taste and stability.

Pirprofen, including its salts, is a medicinal drug having excellent analgesic, antiinflammatory and antipyretic properties; however, it has also an unusually bitter taste and can cause irritation in the gastrointestinal tract. Furthermore, it has a tendency to decompose oxidatively, and pharmaceutical compositions containing Pirprofen or salts thereof are easily discolored, when exposed to heat, light or air. In addition, Pirprofen as the free acid is only slightly soluble in water, so that the manufacture of aqueous pharmaceutical compositions containing it cannot be carried out according to conventional methods and unusual measures have to be taken to obtain stable and compatible aqueous pharmaceutical compositions.

Surprisingly has been found now, that pharmaceutical compositions, which contain a mixture of Pirprofen and a cyclodextrin and/or an inclusion compound of Pirprofen and a cyclodextrin, show markedly improved stability properties, are practically free from the strong bitter taste of Pirprofen itself and cause a much lower incidence of irritation. The improvements can be observed for compositions containing either a mixture of Pirprofen and a cyclodextrin and/or an inclusion compound of Pirprofen and a cyclodextrin.

Furthermore it has been found, that pharmaceutical compositions, which contain (a) a mixture of Pirprofen and a cyclodextrin and/or an inclusion compound of Pirprofen and a cyclodextrin and (b) an effective amount of at least one pharmaceutically acceptable basic substance, are stable and practically tasteless, but in addition are virtually free from causing any irritation whatsoever.

Cyclodextrins, as used in the present invention, represent known cyclic degradation products of starch having 6 to 8 glucose residues in the form of a large ring molecule, of which the α-cyclodextrin has 6, the preferred β-cyclodextrin 7 and the γ-cyclodextrin 8 glucose residues as ring members.

When used in admixture with Pirprofen, the cyclodextrin in the pharmaceutical compositions of the present invention is present in at least equimolar amounts with respect to the active ingredient. Preferably, from about one mole to about 5 moles, advantageously from about 1.5 to about 3.5 moles per one mole of the active ingredient are being used. It has been found, that a large excess of the cyclodextrin has no further improving effect on the properties of the compositions of this invention.

The inclusion compound of Pirprofen and cyclodextrin is a novel compound and represents an additional object of the present invention. It can be formed by contacting Pirprofen with the cyclodextrin in the presence of water. As preferred process modifications for the manufacture of the inclusion compound, there can be mentioned (1) the saturated solution process, which comprises adding water to a mixture of Pirprofen and the cyclodextrin, keeping the aqueous mixture preferably at a temperature of from about 50° to about 60° C. while stirring and then cooling it to precipitate the inclusion compound, (2) the shaking/stirring process, which comprises adding Pirprofen and the cyclodextrin to water, vigorously shaking or stirring the aqueous mixture at about room temperature and collecting the precipitated inclusion compound by filtration, (3) the kneading process, which comprises thoroughly stirring the cyclodextrin together with a relatively small amount of water (for example, with about 1.5 times its weight of water), then adding the Pirprofen to the mixture and thoroughly kneading it to form the inclusion compound, and (4) the neutralization/precipitation process, which comprises preparing an aqueous suspension of the cyclodextrin and Pirprofen, converting the suspension to a solution by rendering its pH basic, for example, by adding an inorganic base, such as an alkali metal, e.g. sodium or potassium, hydrogen carbonate, carbonate or hydroxide, or ammonia, or a solution, particularly an aqueous solution, of such basic substances, stirring the solution, adjusting its pH to about 4 to 5, for example, by adding an inorganic or organic acid, such as a mineral acid, e.g. hydrochloric or sulfuric acid, or a lower alkanoic acid, e.g. acetic acid, and collecting the precipitated inclusion compound by filtration. If desired, a resulting inclusion compound with a higher purity can be obtained by removing any unreacted components, for example, by washing the product with a small amount of a solvent capable of dissolving Pirprofen, such as ethanol, acetone or a 1:1-mixture of ethanol and water.

When producing the inclusion compound, Pirprofen and the cyclodextrin may be used in about equimolar proportions. However, it is advantageous to use the cyclodextrin component in an excess amount, preferably in an amount of from about 1 to about 3 moles per 1 mole of Pirprofen.

As indicated above, the addition of an effective amount of at least one pharmaceutically acceptable basic substance to the pharmaceutical composition containing the mixture of Pirprofen and a cyclodextrin and/or the inclusion compound of Pirprofen and a cyclodextrin causes the residual irritativeness of such compositions to disappear. Useful inorganic basic substances are, for example, alkali metal hydroxides or alkali metal salts of inorganic or organic acids, such as phosphoric or phosphorous acid, carbonic acid, boric acid, acetic acid and the like, such as sodium or potassium hydroxide, lithium, sodium or potassium carbonate or hydrogen bicarbonate, sodium or potassium acetate, di- or tri sodium or -potassium phosphate and the like. Organic basic substances, which may also be used, are e.g. piperazine, amino acids such as lysine, and the like. One may also use mixtures of basic substances, such as a mixture of an alkali metal hydroxide or an alkali metal phosphate.

The effective amount of the basic substance to be added should be an amount, which is sufficient to maintain the medicinal composition system of the present invention at a pH value of about 7 to 8; the amount also depends on the type of the pharmaceutically acceptable basic substance used. The addition of an excessive amount of the latter is undesirable, as it would cause other problems for the composition with respect to its compatibility. For example, from the pharmaceutical point of view, as well as from the viewpoint of the effective elimination of the irritation, it is preferable to add, per 1 mole of Pirprofen, about 1 mole of the basic substance, when as the basic substance sodium hydroxide is used, or from about 0.5 to about 1 mole of sodium hydroxide and from about 0.3 to about 1 mole of disodium phosphate, when the basic substance is represented by a combination of sodium hydroxide and disodium phosphate. Furthermore, one may add from about 0.3 to about 2 moles of trisodium phosphate, or from about 1 to about 2.7 moles of disodium phosphate, or one may use from about 1 to about 1.5 mole of sodium hydrogen carbonate per one mole of Pirprofen.

The pharmaceutical compositions of the present invention, which contain from about 50 mg to about 500 mg of Pirprofen per dosage unit form, may solely consist of the mixture of Pirprofen and a cyclodextrin and/or the inclusion compound of Pirprofen and a cyclodextrin, to which mixture and/or inclusion compound an effective amount of a pharmaceutically acceptable basic substance may be added. However, the pharmaceutical compositions of this invention, which may be in solid or liquid form, for example, in the form of powders (e.g. a so-called dry syrup), small granules, granules, tablets, dragees, capsules, suppositories, suspensions, syrups and the like, preferably contain auxiliary substances, such as excipients, binders, disintegrators, lubricants, flavoring and/or coloring agents and the like. Excipients are, for example, starches, lactose, dextrin, crystalline cellulose, sucrose, glycose, hydroxypropyl starch, calcium hydrogen phosphate, calcium carbonate, magnesium metasilicate-aluminate, aluminum magnesium hydroxide, synthetic aluminum silicate and the like, whereas binders are e.g. starches, crystalline cellulose, agar, sodium alginate, gelatin, gum arabi, traganth gum, guaiac gum, karaya gum, polyvinylpyrrolidone, polyvinyl alcohol, hydroxypropyl-methyl cellulose, carboxymethyl cellulose, hydroxypropyl starch and the like can be used. Disintegrators are e.g. starches, hydroxypropyl starch, carboxymethyl cellulose calcium, crystalline cellulose and the like, and lubricants e.g. talc, magnesium or calcium stearate, synthetic aluminum silicate and the like. As flavoring agents sucrose, licorice root, sorbitol, xylose, mannitol, hydrangea leaves, sodium glycyrrhetinate, lemon oil, vaniline, chocolate orange and the like, and as colorants tar dyestuffs, their lake dyestuffs or iron oxides, conventionally employed in medicinal preparations, are useful. Further additives, which may be used, are e.g. polyoxyethylene fatty acid esters, polyoxyethylene higher alcohol ethers, polyoxyethylene sorbitan fatty acid esters, glycerol fatty acid esters and the like, can be used for the same purposes.

The compositions of the present invention are manufactured according to known methods, the solid compositions, for example, by mixing the active and auxiliary ingredients, if necessary, by granulating such mixtures and/or compressing the mixtures or granules, into tablets, which may be converted into dragees, suppositories by mixing the active ingredients with the appropriate suppository ingredients, and the liquid compositions by dissolving or suspending the active ingredients in the appropriate liquid carriers, such as water and/or ethanol.

The present invention is illustrated in more detail in the following examples, which by no means are limiting on the scope of the invention.

EXAMPLE 1

To one liter of water is added 1.5 g ($6 \times 10^{-3}$ mole) of Pirprofen and 12.8 g ($11.3 \times 10^{-3}$ mole) of $\beta$-cyclodextrin, and the mixture is heated to 50°–60° C. and stirred for 0.5–2 hours. After slowly lowering the temperature to about 20° C. within 6–8 hours, the mixture is allowed to stand at 15°–20° C. for 1–2 days. The precipitate is then collected by filtration and dried at room temperature under reduced pressure to yield 8.62 g of a product with a decomposition point of 226°–231° C.

The infrared absorption spectrum of this product is compared with that of an equimolar mixture of Pirprofen and $\beta$-cyclodextrin. The IR-spectrum reveals, that the absorption at 1690 cm$^{-1}$, assignable to the carboxylic acid residue of the Pirprofen dimer in the equimolar mixture, shifts to 1720 cm$^{-1}$, which bond is assignable to the carboxylic acid residue of the trimer, in which the hydrogen bond is broken due to the inclusion of Pirprofen by $\beta$-cyclodextrin. Furthermore, the differential scanning calorimetric analysis reveales, that the endothermic peak at 95° C., found in the equimolar mixture of Pirprofen and $\beta$-cyclodextrin, has disappeared in the product. Based on these analytical results, the product of this example is identified as the inclusion compound of Pirprofen and $\beta$-cyclodextrin.

EXAMPLE 2

To one liter of water is added 1.5 g ($6 \times 10^{-3}$ mole) of Pirprofen and 12.8 g ($11.3 \times 10^{-3}$ mole) of $\beta$-cyclodextrin, and the mixture is vigorously stirred at room temperature for a period of one week. The resulting precipitate is collected by filtration and dried at room temperature under reduced pressure for 8 hours to yield 5.27 g of a product with a decomposition point of 232°–239° C. Infrared absorption spectrometry and differential scanning calorimetric analysis show the product to be the inclusion compound of Pirprofen and $\beta$-cyclodextrin, identical with the compound of Example 1.

EXAMPLE 3

A total of 60 ml of water is added to 45.4 g (0.04 mole) of $\beta$-cyclodextrin; the mixture is stirred for 0.5–1 hour by means of kneader and then treated with 8.3 g (0.033 mole) of Pirprofen. The mixture is stirred at room temperature for 10 hours, then filtered with suction, and the filter residue is washed with a small amount of a 1:1-mixture of water and ethanol. The insoluble matter is dried under reduced pressure at room temperature to yield 44 g of a product having a decomposition point of 232°–237° C. This product is analyzed by infrared absorption spectrometry and differential scanning calorimetric analysis. The results are identical with those obtained with the product of Example 1, i.e. the product is the inclusion compound of Pirprofen and $\beta$-cyclodextrin.

EXAMPLE 4

To a suspension of 55 g (0.048 mole) of $\beta$-cyclodextrin and 6 g (0.024 mole) of Pirprofen in 2 liters of water is added dropwise a 28% aqueous solution of ammonia while stirring until a homogeneous solution is obtained, which is then stirred for one hour and slowly neutralized with dilute hydrochloric acid until the pH has reached 4.3–4.6. The resulting precipitate is filtered off, washed with a small amount of a 1:1-mixture of water and ethanol, and then dried under reduced pressure at room temperature to yield 22.2 g of a product with a decomposition point of 237°–239° C. Infrared absorption spectrometry and differential scanning calorimetric analysis of the product are identical with those for the product of Example 1; the product is identified as the inclusion compound of Pirprofen and β-cyclodextrin.

EXAMPLE 5

A solution of 2.25 g (0.027 mole) of sodium hydrogen carbonate in 18–30 ml of water is mixed with 41 g (0.036 mole) of β-cyclodextrin and stirred in a mortar for 5–30 minutes. Then, 5 g (0.020 mole) of Pirprofen powder are added, and the mixture is stirred for 1–3 hours. The resulting paste is dried under reduced pressure at 40° C. for 4–8 hours, and the resulting mass is pulverized to yield 48.5 g of a white colored powder, which represents a mixture of Pirprofen, β-cyclodextrin and sodium hydrogen carbonate.

EXAMPLE 6

A solution of 4.5 g (0.032 mole) of sodium hydrogen phosphate in 25–30 ml of water is mixed with 39 g (0.034 mole) of β-cyclodextrin and stirred in a mortar for 5–30 minutes, after which 5 g (0.020 mole) of Pirprofen powder is added. Stirring is continued for 1–3 hours. The resulting paste is dried under reduced pressure at 40° C. for 4–8 hours and then pulverized to yield 47 g of a powdered material, which represents a mixture of Pirprofen, β-cyclodextrin and sodium hydrogen phosphate.

EXAMPLE 7

A mixture is prepared by adding 80 mg of piperazine hexahydrate to 100 mg of Pirprofen and 820 mg of β-cyclodextrin, which is thoroughly homogenized. A suspension of the mixture is obtained by adding 10 ml of water to the powder, which consists of Pirprofen, β-cyclodextrin and piperazine.

EXAMPLE 8

A granulate powder containing 6.66% of Pirprofen can be manufactured as follows:

| Ingredients (for 1500 g) | |
| --- | --- |
| Pirprofen | 100 g |
| β-cyclodextrin | 775 g |
| sodium hydrogen carbonate | 40 g |
| lactose | 585 g |

The above components are thoroughly mixed to yield a homogenous mixture and the latter is processed, using a dry-granule method to yield the derived granulated powder, containing 100 g of Pirprofen per 1500 g of granulate.

EXAMPLE 9

Capsules, containing 411 mg of the inclusion compound of Pirprofen and β-cyclodextrin as described in Example 1, are prepared as follows:

| Ingredients (for 5000 capsules) | |
| --- | --- |
| Inclusion compound of Pirprofen and β-cyclodextrin (Example 1) | 2055 g |
| crystalline cellulose | 285 g |
| hardened cotton-seed oil | 15 g |

The above mentioned components are mixed to a homogeneous mixture and 471 mg of the mixture are filled into capsules, each containing the equivalent of 52 mg of Pirprofen.

EXAMPLE 10

Tablets, containing 205 mg of the inclusion compound of Pirprofen and β-cyclodextrin as described in Example 1, are prepared as follows:

| Ingredients (for 4000 tablets) | |
| --- | --- |
| Inclusion compound of Pirprofen and β-cyclodextrin (Example 1) | 820 g |
| lactose | 1108 g |
| calcium salt of carboxymethyl-cellulose | 260 g |
| hardened cotton-seed oil | 12 g |

The tablets, each weighing 550 mg, are prepared according to conventional methods and contain the equivalent of 24.9 mg of Pirprofen.

EXAMPLE 11

A dry syrup, containing 102 mg of Pirprofen per 1 g, can be prepared as follows:

| Ingredients | |
| --- | --- |
| Pirprofen | 15.00 g |
| β-cyclodextrin | 116.25 g |
| sodium hydrogen carbonate | 6.00 g |
| sodium salt of carboxymethyl-cellulose | 1.80 g |
| crystalline cellulose | 7.95 g |

To the β-cyclodextrin are added the sodium hydrogen carbonate and an adequate amount of water, followed by Pirprofen. The mixture is stirred at room temperature for several hours, an approved pigment, a suitable amount of a binding agent, the sodium carboxymethylcellulose are added to the mixture. The dry-syrup is prepared according to a wet-granulating method; it contains 102 mg of Pirprofen in 1 g of the dry-syrup mixture.

TEST EXAMPLE 1

The inclusion ratio of Pirprofen to β-cyclodextrin in the inclusion compounds of Examples 1 to 4 is measured by the continuous change method, which is based on the difference of the absorbence in the ultraviolet region between the solution of the inclusin compound and solution of Pirprofen itself. Thus, while changing the quantities of Pirprofen and β-cyclodextrin continuously by using a 0.1 molar phosphate buffer solution (pH 7.0, 19° C.), the difference in absorbence in the ultraviolet region is measured at a wavelength of λ=253 nm. The results obtained are shown in FIG. 1. These results suggest, that a mixture of Pirprofen and β-cyclodextrin of a molar ratio of 1:1 shows the greatest change of the UV absorbence.

FIG. 1 illustrating the difference in absorbence in the ultraviolet region as a function of the composition ratio between β-cyclodextrin and Pirprofen.

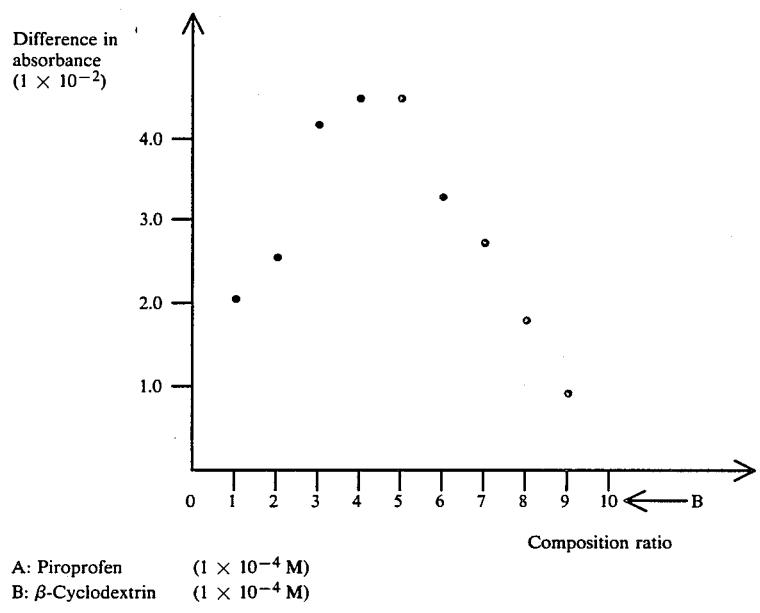

A: Piproprofen   (1 × 10⁻⁴ M)
B: β-Cyclodextrin (1 × 10⁻⁴ M)

TEST EXAMPLE 2

Stability Tests 2.1 About 3 g of Pirprofen powder, about 3 g of the inclusion compound as described in Example 1 and about 3 g of the inclusion compound as described in Example 2 are placed on respective dishes, having a diameter of 4 cm, and allowed to stand for one week in a desiccator with a controlled temperature of 60° C. and a controlled humidity of 75%, after which the state of discoloration of the samples was visually evaluated.

2.2 2 g of Pirprofen powder, 2 g of the inclusion compound as described in Example 1 and 2 g of the inclusion compound as described in Example 2 are sealed into respective bags made of polyvinyl chloride resin and irradiated with a xenon lamp for 24 hours, after which the state of discoloration of the samples was visually evaluated.

The results of the tests are summarized in Table 1.

TABLE 1

| | Conditions | |
|---|---|---|
| Samples | After standing for one week at 60° C. at a humidity of 75% | After irradiation for 24 hours with a xenon lamp |
| Pirprofen powder | light brown | brown |
| Inclusion compound of Example 1 | white | white |
| Inclusion compound of Example 2 | white | white |

2.3. Stability tests are carried out by repeating the procedures of Test Examples 2.1 and 2.2, except that the powder described in Example 5 is used as test sample. The results are shown in Table 2.

TABLE 2

| | Conditions | |
|---|---|---|
| Sample | After standing for one week at 60° C. at a humidity of 75% | After irradiation for 24 hours with a xenon lamp |
| Pirprofen powder | brown | yellow |
| Powder of Example 5 | slightly yellowish-white | very slight yellow |

TEST EXAMPLE 3

Acceptability Test 3.1. Two samples, one by suspending about 1 g of the inclusion compound as described in Example 3 (containing 100 mg of Pirprofen) in 10 ml of water, and the other by suspending a mixture consisting of 100 mg of Pirprofen and 30 mg of carboxylmethyl-cellulose (as a suspension stabiliser) in 10 ml of water, are prepared. An acceptability test with respect to bitterness and irritation is carried out by giving 2 to 3 ml of each sample to seven healthy male persons. The results are summarized in Table 3. The results of the assessment are expressed by way of numerical figures, ranging from 0 to 10, with 0 expressing an irritation, which prevents the acceptance of the sample, increasing numbers expressing a correspondingly diminishing irritation, and 10 expressing no irritation at all.

| Assessment Sample | No. of persons giving the assessment | | | | | | | | | | |
|---|---|---|---|---|---|---|---|---|---|---|---|
| | 0 | 1 | 2 | 3 | 4 | 5 | 6 | 7 | 8 | 9 | 10 |
| Aqueous suspension of Pirprofen | 7 | | | | | | | | | | |
| Inclusion compound of Example 3 | | | | | 4 | 2 | 1 | | | | |

3.2. About 1 g of the powder described in Example 5 is suspended in 10 ml of water; 1 g of the powder contains about 100 mg of Pirprofen. An acceptance test with respect to bitterness and irritation is carried out by giving 2 to 3 ml of the suspension to seven healthy male persons. The results are summarized in Table 4. In the same manner as in Test Example 3.1., the results of the assessment are expressed by numerical figures from 0 to 10.

TABLE 4

| Assessment | 0 | 1 | 2 | 3 | 4 | 5 | 6 | 7 | 8 | 9 | 10 |
|---|---|---|---|---|---|---|---|---|---|---|---|
| Powder of Example 5 (persons) | | | | | | | | | 1 | 5 | 1 |

3.3. An acceptance test with both, the powder and the suspension described in Example 7, is carried out according to the method described under 3.1. and 3.2., by using seven healthy male volunteers. Both, the powder and the suspension, give a mean assessment value for all 7 persons of 8 to 9, which demstrates, that the irritation had been abolished to a great extent.

3.4. Samples having the ingredient ratios shwon in Table 5, are prepared and each sample is homogenized in a mortar for 3 minutes, then subjected to the acceptance test using seven healthy male volunteers. The results of the assessment are expressed by the mean value for the seven volunteers, with the numerical figures of 0 to 10 used in the same manner as under 3.1.

TABLE 5

| Ingredients (mg) | Sample No. | | | | | |
|---|---|---|---|---|---|---|
| | 1 | 2 (Control) | 3* | 4 | 5 | 6 (Control) |
| Pirprofen | 100 | 100 | 100 | 100 | 100 | 100 |
| disodium hydrogen phosphate | | | | 90 | 45 | 90 |
| sodium hydrogen carbonate | | | | | 45 | |
| β-cyclodextrin | 815 | | 815 | 775 | 775 | |
| lactose | | 815 | | | | 775 |
| Assessment of the acceptance test | 6-7 | 0-1 | 7-8 | 8-9 | 9-10 | 1-2 |

(*sample No. 3 is prepared by kneading the ingredients together with water and drying the kneaded mixture)

It is apparent from the above-mentioned results, that β-cyclodextrin used according to the present invention lessens the irritation causing effects of Pirprofen in an entirely different manner than conventional excipients.

TEST EXAMPLE 4

Stability Constant (Kc)

The pH profile of the stability constant (Kc) of Pirprofen-β-Cyclodextrin inclusion complex has been determined as follows:

In the Pirprofen-β-cyclodextrin inclusion complex stability constant (Kc) can be obtained from the Scott's equation[1] with the difference of ultraviolet absorbance of Pirprofen in the absence and presence of different amount of β-cyclodextrin[2].

Reference:
(1) Scott's equation
$a.b/d = 1/Kc.\epsilon c + b/\epsilon c$
a: concentration of Pirprofen
b: concentration of β-cyclodextrin
c: difference of UV absorbance between free and complexed Pirprofen
$\epsilon c$: the difference of molar absorptive coefficient between free and complex Pirprofen
kc: stability constant of Pirprofen-β-cyclodextrin inclusion complex (2) Experimental condition
The difference of UV absorbance between absence and presence of β-cyclodextrin was measured at 253 nm (pH 5-12) and 260 nm (pH 1.6-4.5).

The pH profile for the stability constant (Kc) can be made by plotting the log Kc against pH values (see Sketch A). This pH profile indicates that the inclusion complex is most stable at pH 7.5.

These facts support the innovative characteristics in the invention that β-cyclodextrin can improve effectively the irritant bitterness of Pirprofen in the presence of weak basic substances (ex. NaHCO$_3$, Na$_2$HPO$_4$) and that the irritant bitterness of Pirprofen is effectively reduced by strong inclusion complexation of β-cyclodextrin at pH 7.5.

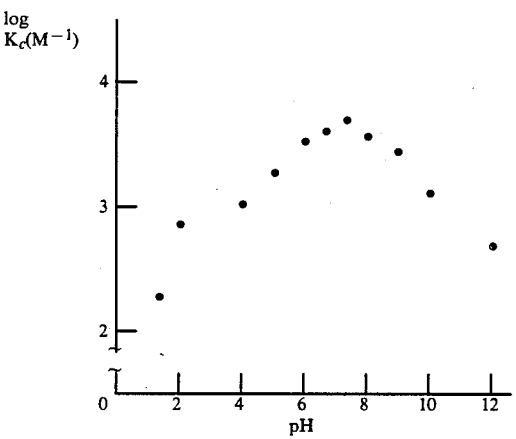

Sketch A

The pH Profile for the Stability Constant ($K_c$) of PF—β-CyD Complex

We claim:
1. A pharmaceutical composition comprising an analgesic, antiinflammatory and antipyretic effective amount of an inclusion compound of α-[3-chloro-4-(3-pyrrolin-1-yl)-phenyl]-propionic acid and a cyclodextrin, and a pharmaceutically acceptable carrier.

2. A composition according to claim 1, wherein said pharmaceutically acceptable carrier comprises at least one pharmaceutically acceptable inorganic or organic basic substance.

3. A composition according to claim 2 wherein said basic substance is a member selected from the group consisting of an alkali metal hydroxide, phosphate, phosphite, carbonate, hydrogen carbonate, borate, and acetate; a basic amino acid; and piperizine.

4. A composition according to claim 2, wherein said pharmaceutically acceptable inorganic basic substance is a member selected from the group consisting of an alkali metal hydroxide, phosphate, phosphite, carbonate, hydrogen carbonate, borate and acetate.

5. A composition according to claim 2, wherein said pharmaceutically acceptable organic basic substance is a member selected from the group consisting of a basic amino acid and piperazine.

6. A method of treating pain comprising administering an analgesic, antiinflammatory and antipyretic effective amount of the composition according to claim 1, to a patient in need of the same.

7. A method of treating fever comprising administering an analgesic, antiinflammatory and antipyretic effective amount of the composition according to claim 1, to a patient in need of the same.

8. A method according to claim 6, wherein said composition contains a pharmaceutically acceptable carrier comprising at least one pharmaceutically acceptable inorganic or organic basic substance.

9. A method according to claim 7, wherein said composition contains a pharmaceutically acceptable carrier comprising at lest one pharmaceutically acceptable inorganic or organic substance.

10. A method according to claim 8 wherein said basic substance is a member selected from the group consisting of: an alkali metal hydroxide, phosphate, phosphite, carbonate, hydrogen carbonate, borate and acetate; a basic amino acid; and piperazine.

11. A method according to claim 9, wherein said basic substance is a member selected from the group consisting of: an alkali metal hydroxide, phosphate, phosphite, carbonate, hydrogen carbonate, borate and acetate; a basic amino acid; and piperazine.

12. An inclusion compound of α-[3-chloro-4-(3-pyrrolin-1-yl)-phenyl]-propionic acid and a cyclodextrin.

13. An inclusion compound according to claim 12, wherein said cyclodextrin is β-cyclodextrin.

* * * * *